United States Patent [19]

Vedage et al.

[11] Patent Number: 5,360,934
[45] Date of Patent: Nov. 1, 1994

[54] HYDROGENATION OF AROMATIC AMINES TO PRODUCE THEIR RING HYDROGENATED COUNTERPARTS

[75] Inventors: Gamini A. Vedage, Bethlehem; John N. Armor, Orefield, both of Pa.

[73] Assignee: Air Products and Chemicals, Inc., Allentown, Pa.

[21] Appl. No.: 83,843

[22] Filed: Jun. 25, 1993

[51] Int. Cl.$^5$ ............... C07C 209/72; C07C 211/26; B01J 23/40; B01J 21/04
[52] U.S. Cl. .................. 564/451; 564/452; 564/450; 564/306; 502/325; 502/326
[58] Field of Search ............... 564/451, 450, 452, 306; 502/325, 326

[56] References Cited

U.S. PATENT DOCUMENTS

| | | | |
|---|---|---|---|
| 2,511,028 | 6/1950 | Whitman | 564/305 |
| 2,606,924 | 8/1952 | Whitman | 564/450 |
| 2,606,925 | 8/1952 | Whitman | 564/449 |
| 2,606,928 | 8/1952 | Barkdoll et al. | 564/451 |
| 3,155,724 | 11/1964 | Arthur | 564/444 |
| 3,347,917 | 10/1967 | Arthur | 564/444 |
| 3,591,635 | 7/1971 | Farrissey | 564/451 |
| 3,644,522 | 2/1972 | Brake et al. | 564/450 |
| 3,679,746 | 7/1972 | Brake | 564/444 |
| 3,696,108 | 10/1972 | Morikawa | 585/436 |
| 3,711,550 | 1/1973 | Brake | 564/444 |
| 3,766,272 | 10/1973 | Brake | 564/444 |
| 4,034,061 | 7/1977 | McArthur | 423/213.5 |
| 4,220,559 | 9/1980 | Polinski | 252/455 R |
| 4,946,998 | 8/1990 | Casey et al. | 564/451 |
| 4,960,941 | 10/1990 | Vedage et al. | 564/450 |
| 5,116,879 | 5/1992 | Eri et al. | 518/716 |

FOREIGN PATENT DOCUMENTS 1122609 8/1968 United Kingdom .

Primary Examiner—Glennon H. Hollrah
Assistant Examiner—Deborah Lambkin
Attorney, Agent, or Firm—Russell L. Brewer; James C. Simmons; William F. Marsh

[57] ABSTRACT

This invention relates to an improved hydrogenation process wherein aromatic amines are hydrogenated to their ring hydrogenated counterparts. These aromatic amines are presented by the formulas:

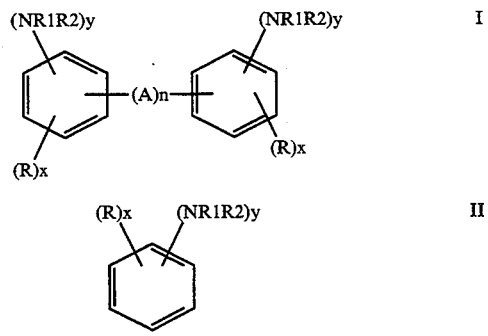

wherein R is hydrogen or $C_{1-6}$ aliphatic, R1 and R2 are hydrogen or $C_{1-6}$ aliphatic, A is $C_{1-4}$ or NH; n is 0–2, x is 1–3 and y is 1 to 2 except the sum of the y groups in Formula I may be 1. The improvement resides in the utilization of a catalyst comprising rhodium carried on a support of kappa, theta or delta alumina.

23 Claims, 1 Drawing Sheet

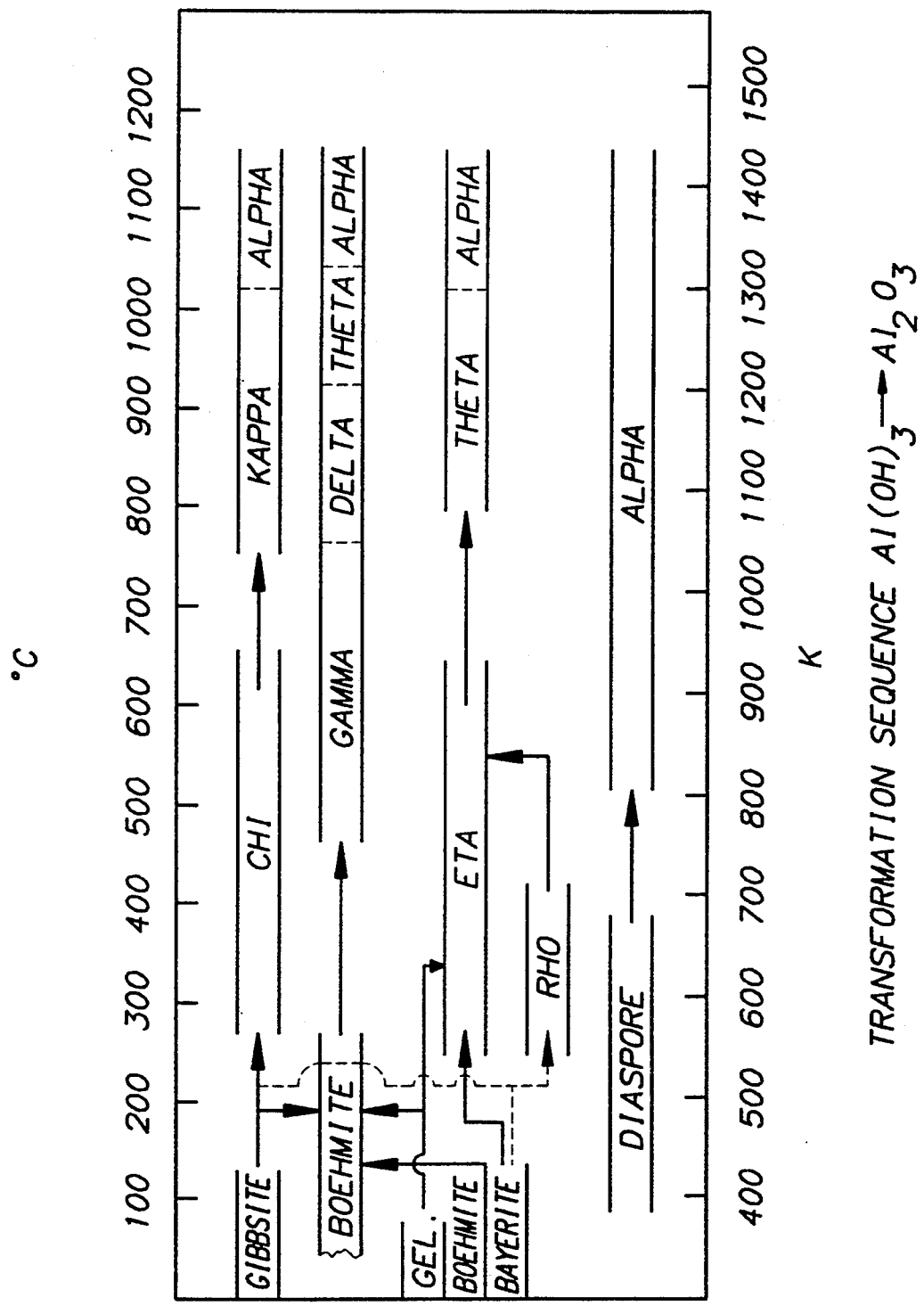

HYDROGENATION OF AROMATIC AMINES TO PRODUCE THEIR RING HYDROGENATED COUNTERPARTS

TECHNICAL FIELD

This invention pertains to a process for hydrogenating aromatic amines to produce their ring hydrogenated counterparts.

BACKGROUND OF THE INVENTION

There is substantial literature in the art with respect to the hydrogenation of aromatic amines, including bridged aromatic amines, e.g., methylenedianiline to produce 4,4'-methylenedi(cyclohexylamine), also called bis(para-aminocyclohexyl)methane, bis (4-aminocyclohexyl)methane and PACM.

Some of the early hydrogenation work to produce aromatic amines, such as, PACM, was done by Whitman and Barkdoll, et al. and their work is set forth in a series of U.S. Pat. Nos., e.g., 2,511,028; 2,606,924; 2,606,925; and 2,606,928. Basically the processes described in these patents involve the hydrogenation of methylenedianiline at pressures in excess of 200 psig, preferably in excess of 1,000 psig, at temperatures within a range of 80° to 275° C. utilizing a ruthenium catalyst. The hydrogenation is carried out under liquid phase conditions and an inert organic solvent is used in the hydrogenation process. Typically, a liquid product having a trans, trans- isomer content of 15-23% is obtained. Examples of ruthenium catalysts utilized for the hydrogenation process include ruthenium oxides such as ruthenium sesquioxide and ruthenium dioxide; and ruthenium salts.

Brake, et al. in U.S. Pat. Nos. 3,696,108 and 3,644,522 continued in the development of processes for manufacturing PACM by hydrogenating methylenedianiline. They found that if the ruthenium was carried upon a support and the support was alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation.

U.S. Pat. Nos. 3,347,917; 3,711,550; 3,679,746; 3,155,724; 3,766,272 and British Patent 1,122,609 disclose various isomerization processes and hydrogenation processes to produce PACM containing high trans,trans- isomer content; i.e. an isomer content near equilibrium typically 50% trans,trans-, 43% cis,trans- and 7% cis,cis-. As in the early work ruthenium catalysts usually were used to effect isomerization. High temperatures and longer reaction times were required to produce the high trans,trans- product and, in addition, considerable deamination of product took place.

A wide variety of catalytic systems have been developed for the hydrogenation of aromatic amines, and typical catalytic systems are represented in the following patents:

U.S. Pat. No. 3,591,635 discloses the use of rhodium on alumina as a catalyst for the hydrogenation of methylenedianiline.

U.S. Pat. No. 4,946,998 discloses processes for the hydrogenation of methylenedianiline contaminated with impurities utilizing a mixture of rhodium and ruthenium on alumina as the catalyst. A hydrogenated methylenedianiline product having a trans, trans- isomer content of from about 14 to 28% is prepared using the mixed metal catalyst system, although higher trans, trans- isomer content can be achieved through high temperature, long reaction times, and high ruthenium concentration. The presence of rhodium permits lower operating temperatures and reduces the percent trans, trans- isomer.

U.S. Pat. No. 4,960,941, similar to U.S. Pat. No. 4,946,998 and disclose the hydrogenation of crude methylenedianiline containing up to about 15% oligomers using a mixed metal catalyst system. The catalyst comprises rhodium and ruthenium, the '941 patent showing a preference for the rhodium being carried on a titania support.

DRAWING

The drawing is a plot of the phases of alumina as a function of temperature.

SUMMARY OF THE INVENTION

This invention relates to an improved process for producing aromatic amines such as 4,4'-methylenedi(cyclohexylamine) (PACM) by the catalytic hydrogenation of such aromatic amines to produce their hydrogenated counterparts. The improvement in the hydrogenation process comprises using a catalytic system comprising rhodium carried on an alumina support, said alumina being selected from the group consisting of kappa, theta, and delta. As a catalyst the weight ratio of rhodium to select alumina support, calculated on metal content, generally is from 1 to 25 weight parts rhodium per 100 weight parts alumina.

There are several advantages associated with this process. These include:

- an ability to produce a ring hydrogenated counterpart to the aromatic amine in high selectivity;
- an ability to effect hydrogenation of aromatic amines at relatively low pressures, e.g., 1500 psig and lower via a highly active catalyst at excellent reaction rates;
- an ability to hydrogenate bridged aromatic amines without effecting significant deamination of the feed or product; and,
- an ability to use the catalyst for continued periods of time with only modest maintenance or regeneration techniques.

DETAILED DESCRIPTION OF THE INVENTION

This invention relates to an improvement in the conventional ring hydrogenation of aromatic amines and these amines are represented by the formulas:

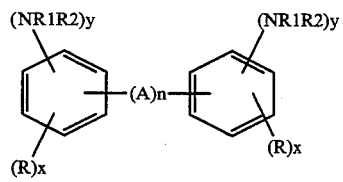

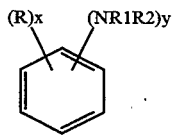

wherein R is hydrogen or $C_{1-6}$ aliphatic, R1 and R2 are hydrogen, or $C_{1-6}$ aliphatic, A is $C_{1-4}$ alkyl, or NH, n is 0 or 1, x is 1–3 and y is 1–2 except the sum of the y groups in Formula I may be 1. By the practice of this invention, one is able to selectively produce a ring hydrogenated reaction product in high selectivity with excellent reaction rates.

The aromatic amines useful in the practice of the process are bridged polynuclear aromatic amines or mononuclear aromatic amines. These can be substituted with various substituents such as aliphatic groups containing from 1–6 carbon atoms. Further, the amine group can be substituted with aliphatic groups such as alkyl or alkanol groups resulting in secondary and tertiary amine substituents. Examples of bridged aromatic amines include methylene dianilines such as bis(para-aminophenyl)methane (MDA) including up to about 15% aniline oligomers by weight; bis(diaminophenyl)methane; bis(para-amino-2-methylphenyl)methane; bis(diaminophenyl)propane; biphenylamine; tolidine; $N-C_{1-4}$-aliphatic derivatives and $N,N'C_{1-4}$ aliphatic secondary and tertiary amine derivatives of the above bridged aromatic amines. Examples of mononuclear aromatic amines include 2,4- and 2,6-toluenediamine, alkylated derivatives of toluenediamine, such as, 1-methyl-3,5-diethyl-2,4 or 2,6-diaminobenzene, commonly known as diethyltoluenediamine; diisopropyltoluenediamine, mono-isopropyl toluenediamine, tert-butyl-2,4- and 2,6-toluenediamine, cyclopent-toluenediamine; phenylenediamine, aniline, and alkylated derivatives of phenylenediamine and aniline, e.g., ortho-toluidine, ethyl toluidine, xylenediamine, mesitylene diamine, and the N and $N,N'C_{1-4}$ aliphatic secondary and tertiary amine derivatives of the mononuclear aromatic monoamines and mononuclear aromatic diamines.

The hydrogenation process is carried out under liquid phase conditions, such liquid phase conditions being maintained typically by carrying out the hydrogenation in the presence of a solvent. Although as reported in the art, it is possible to produce the reaction product in the absence of a solvent, the processing usually is much simpler when a solvent is employed. Representative solvents suited for practicing the invention include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred. Although in some processes water can be used as a cosolvent, it is preferred that the system be maintained in an anhydrous state or at least maintained such that the water concentration is less than 0.5% by weight. Water, when present in the system, tends to increase the amount of by-product alcohols and heavy condensation products and it tends to deactivate the catalyst system.

When a solvent is used, concentrations as low as 50% by weight based upon the aromatic amine introduced into the reaction zone are common and typically the solvent is used at levels from about 75 to about 500% by weight of the starting compound. High solvent use has associated recovery burdens.

The hydrogenation is carried out principally in a batch process although it is possible to operate the plant continuously. Temperatures usually used for the hydrogenation process range from about 130° to 220° C. with preferred temperatures of from about 170° to 195° C. Pressures as low as from about 200 to 1500 psig, even with systems containing impurities such as oligomers of MDA can be used thus providing for lower equipment costs and operating costs. When the pressure is raised toward the upper end of the operating range, higher reaction rates may be achieved.

The rhodium metal, as is the ruthenium metal when used, is carried on a select alumina support generally in a ratio of about 0.5 to 25 weight parts rhodium per 100 weight parts of support, preferably 1 to 12 weight parts metal per 100 weight parts support. At these levels a catalyst level from 0.1 to 104 by weight of the aromatic amine is utilized with preferred levels being from 0.5 to 5% by weight. When the amount of catalyst approaches the lower limit of the range, the reaction rate may decrease. However, as the concentration of catalyst vis-a-vis the aromatic amine increases the reaction rate will increase up to a point and then level off to a constant rate.

A preferred catalyst system comprises rhodium and another hydrogenation catalyst, typically ruthenium. In a rhodium/ruthenium catalyst system the ratio of rhodium to ruthenium is from about 1 to 12, preferably 3 to 8 weight parts rhodium per weight part alumina. Generally each metal is carried on a separate support. This catalyst system permits kinetic control of the reaction at low pressures, with the advantage that there is excellent selectivity with an excellent reaction rate.

The support is key to the catalyst system in that at least the rhodium component is carried on a support selected from kappa, delta, and theta alumina. Kappa-alumina is the preferred alumina. These aluminas has are obtained by a high temperature calcination of alumina oxides or their gel s from 700° C. to 1000° C. The drawing correlates temperature with the phases of alumina and can be used as a reference. Other aluminas, such as gamma-alumina which have been used in the past, do not afford the high activity and long life.

The progress of a hydrogenation reaction can readily be followed by observing the amount of hydrogen taken up by the reaction mixture and the reaction is terminated when the amount of hydrogen consumed is equal or nearly equal to that amount necessary to effect complete hydrogenation to product. In general, the hydrogenation time for aromatic amines will range from about 100 to 500 minutes, at modest catalyst levels, e.g., 0.5–5% broadly 0.1–10% by weight of the aromatic amine at 180° C. and 850 psi pressure, and generally will not exceed 500 minutes.

Although not intending to be bound by theory, it is believed the unexpected activity and life of the catalyst system is due to the enhanced surface area of the rhodium when dispersed on the support.

The following examples are intended to illustrate various embodiments of the invention and all parts and percentages given are weight parts or weight percents unless otherwise specified.

EXAMPLE 1

Rhodium and Ruthenium Catalyst Preparation a. Preparation of 2.8% Rh/kappa-$Al_2O_3$ Catalyst Four grams of $Rh(NO_3)_3$ (10 weight % Rh) solution was added to 300 cc of deionized (DI) water. This solution had a pH of 2.1. The pH of this solution was increased to between 3.8–4.2 by adding $NH_4OH$ dropwise. To that solution was added 10 g of kappa-alumina (identified by x-ray diffraction), and the mixture stirred for 5 min. The pH of this solution was then increased to 8.5 by adding NH$_4$OH in a dropwise manner. Once the pH reached 8.5, the mixture was stirred for an additional 15 min and the mixture was filtered through Watman filter paper. The filtrate was yellow orange in color indicating that all the rhodium was not deposited. The filtered solid was dried in a hood overnight and was calcined at 400° C. for 3 hrs in air to obtain the final catalyst. When analyzed for rhodium content this catalyst had 2.8% Rh.

b. Preparation of 2.2% Rh/kappa-Al$_2$O$_3$ Catalyst

Three grams of Rh(NO$_3$)$_3$ (10 weight % Rh) solution was added to 300 cc of deionized (DI) water. This solution had a pH of 2.1. The pH of this solution was increased to between 3.8–4.2 by adding NH$_4$OH dropwise. To that solution was added 10 g of kappa-alumina (identified by x-ray diffraction), and the mixture stirred for 5 min. The pH of this solution was then increased to 8.5 by adding NH$_4$OH in a dropwise manner. Once the pH reached 8.5, the mixture was stirred for an additional 15 min and the mixture was filtered through Watman filter paper. The filtrate was yellow orange in color indicating that all the rhodium was not deposited. The filtered solid was dried in a hood overnight and was calcined at 400° C. for 3 hrs in air to obtain the final catalyst. When analyzed for rhodium content this catalyst had 2.2% Rh.

c. Preparation of 1% Rh/kappa-Al$_2$O$_3$ Catalyst

One gram of Rh(NO$_3$)$_3$ (10 weight % Rh) solution was added to 3 gms of DI water. To this solution was added 10 grams of kappa-alumina (identified by x-ray diffraction), and the solid mixed well with the solution. The catalyst was dried overnight and calcined at 400° C. for 3 hrs in air to obtain the final catalyst. When analyzed for rhodium this catalyst had 1% Rh.

d. Preparation of 2% Rh/alpha-Al$_2$O$_3$ Catalyst

The method of preparation was the same as (a) with the exception of using 10 grams of alpha-alumina catalyst. This catalyst had 2% Rh.

e. Preparation of Rh/Al$_2$O$_3$ Catalysts

Four grams of Rh(NO$_3$)$_3$ (10 weight % Rh) solution was added to 300 cc of deionized (DI) water. This solution had a pH of 2.1. The pH of this solution was increased to between 3.8–4.2 by adding NH$_4$OH dropwise. To that solution was added 10 g of alumina (type of alumina is given below) and the mixture stirred for 5 min. The pH of this solution was then increased to 8.5 by adding NH$_4$OH in a dropwise manner. Once the pH reached 8.5, the mixture was stirred for an additional 15 min and the mixture was filtered through Watman filter paper. The filtrate was colorless indicating all rhodium was deposited. The filtered solid was dried in a hood overnight and was calcined at 400° C. for 3 hrs in air to obtain the final catalyst. The rhodium content of these catalysts are given below.

| Supplier of Support | Phase of Alumina | % Rh |
|---|---|---|
| Versal GH from LaRoche Chemicals Inc. | gamma | 3.6 |
| Heat treated Versal GH | delta | 3.7 |
| Theta-100 from Alcoa Corporation | theta | 2.8[a] |
| Heat treated gibbsite | chi | 3.8 |
| Heat treated Bayerite | eta | 4.1 |

[a] filtrate was orange in color indicating that all the rhodium did not deposit on Al$_2$O$_3$

EXAMPLE 2

Catalyst Prereduction Technique

1. Catalyst Pretreatment-Autoclave

Prior to catalyst use, the catalyst was prereduced before use as outlined below to reduce the impact of catalyst preparation and storage history. The catalyst was charged to an empty, clean 300 cc or 1 liter autoclave reactor and THF was added to the reactor. The autoclave was then sealed, leak tested and purged three times with nitrogen (pressurize to >200 psig, agitated, then vented to atmospheric pressure with the agitator off). The reactor was then purged three times with hydrogen (as with nitrogen but pressurized to 850 psig) and then pressurized to 650 psig. The reactor was then heated to 192° C. and once at temperature, the reactor pressure was adjusted to 850 psig. The system was held at temperature for two hours, cooled, vented and purged three times with nitrogen. The catalyst was recovered by filtering the mixture under nitrogen atmosphere.

EXAMPLE 3

Catalyst Comparison in MDA Hydrogenation

Hydrogenation Procedure-General

A 300 cc autoclave reactor or a 1-liter reactor was used during this work. All hydrogenations were carried out at 1500 rpm stirring rates to minimize hydrogen mass transfer as a limitation to reaction rates. The desired pre-reduced catalyst charge from Example 1 was weighed and added to the pressure vessel. The feed was then added to the reactor. Any desired base (e.g. LiOH) was added as a 10% water solution to the reactor. The reactor was closed, leak tested and purged three times with nitrogen and then purged three times with hydrogen. The reactor was pressurized with hydrogen to 650 psig and heated to desired reaction temperature with agitation. When reaction temperature was reached, the reactor pressure was adjusted to 850 psig. The reactor was connected through a pressure controller to a ballast tank filled with hydrogen. The volume and hydrogen pressure of the ballast tank was chosen to be sufficient to provide all the hydrogen necessary for the reaction without dropping below 1000 psi. The volume was also small enough so that the ballast pressure drop during the reaction gave an accurate measure of the hydrogen consumed. The ballast pressure was followed versus time as a measure of the hydrogenation taking place. By calculating, the ballast pressure change (known volume), the molar hydrogen consumption was determined. When the reaction test was completed, the ballast line was closed, the reactor was cooled and the reactor was purged with nitrogen. The reaction mixture was then removed through the charge line/filter. Life studies in Examples to follow were done by adding the feed through the charge line/filter and repeating the procedure. Table 1 notes catalyst type, reaction conditions and yield. Table 2 provides results for the catalytic hydrogenation of MDA-100 referring to 100% MDA.

TABLE 1

HYDROGENATION OF METHYLENEDIANILINE
Catalyst Activity and Selectivity Data
Hydrogenation of 50% MDA/THF at 180° C. and 850 psi pressure using
a physical mixture of Rh/Al$_2$O$_3$ and 5% Ru/Al$_2$O$_3$ catalysts (RH:Ru = 7:1)

| Run | Catalyst | Phase of Alumina | Catalyst Weight (Rh/Al$_2$O$_3$) as a % of MDA | Conversion (%) | Reaction Time (min)$^a$ | PACM (%) | ½ PACM (%) | MDA (%) | Deaminated Product (%) | Secondary Amines (%) |
|---|---|---|---|---|---|---|---|---|---|---|
| 1 | 3.8% Rh/chi-Al$_2$O$_3$ | chi-Al$_2$O$_3$ | 1.5 | 79 | 220 | 38.2 | 38.2 | 1.5 | 2.6 | 19.4 |
| 2 | 4.1% Rh/eta-Al$_2$O$_3$ | eta-Al$_2$O$_3$ | 1.5 | 57 | 220 | 17.2 | 51.0 | 17.5 | 1.3 | 12.9 |
| 3 | 3.6% Rh/gamma-Al$_2$O$_3$ | gamma-Al$_2$O$_3$ | 1.5 | 99 | 150 | 76.2 | 2.6 | 0.0 | 2.1 | 19.0 |
| 4 | 4% Rh/Al$_2$O$_3$$^b$ | gamma-Al$_2$O$_3$ | 1.5 | 99 | 145 | 82.5 | 2.1 | 0.0 | 1.7 | 13.8 |
| 5 | 2.8% Rh/theta-Al$_2$O$_3$ | theta-Al$_2$O$_3$ | 2.1 | 99 | 125 | 78.8 | 2.2 | 0.0 | 1.8 | 17.2 |
| 6 | 3.7% Rh/delta-Al$_2$O$_3$ | delta-Al$_2$O$_3$ | 1.5 | 99 | 120 | 82.5 | 2.4 | 0.0 | 1.8 | 13.3 |
| 7 | 2.8% Rh/kappa-Al$_2$O$_3$ | kappa-Al$_2$O$_3$ | 2.1 | 100 | 65 | 82.5 | 0.0 | 0.0 | 1.5 | 16.0 |
|  | 2.0% Rh alpha-Al$_2$O$_3$ | alpha-Al$_2$O$_3$ | 3.0 | 99 | 135 | 80.5 | 1.1 | 0.0 | 2.4 | 16.0 |

$^a$Time for conversion except with chi and eta alumina.
$^b$Purchased from Engelhard Corporation.

Table 1 shows the activity of Rh/A$_2$O$_3$ catalyst as a function of the phase of alumina. Although the same technique was used to prepare all these catalysts the level of rhodium for theta, kappa, delta, gamma, and alpha alumina catalysts were different. Therefore, the amount of catalyst was adjusted based on MDA so that the activities can be compared on an equal rhodium basis.

The catalysts based on chi and eta alumina (Runs 1 & 2) had very low activity while the catalysts based on delta, theta and kappa was more active than a commercial gamma-alumina type catalyst. The rhodium on kappa-alumina catalyst had the highest activity. On an equivalent rhodium basis 2.8% Rh/kappa-A$_2$O$_3$ catalyst was about twice as active as the commercial 4% Rh/A$_2$O$_3$ gamma supported catalyst. As shown in Table 1 the catalyst activity decreases in the order. Rh/kappa-Al$_2$O$_3$>Rh/delta-Al$_2$O$_3$/Rh/theta-Al$_2$O$_3$>commercial gamma-alumina type catalyst/Rh/gamma-Al$_2$O$_3$/Rh/alpha-Al$_2$O$_3$>Rh/chi-Al$_2$O$_3$>Rh/eta-Al$_2$O$_3$.

TABLE 2

Effect of Rhodium Loading on Activity of Kappa Alumina Catalyst
Hydrogenation of 50% MDA/THF$^a$ at 180° C. and 850 psi pressure using
a physical mixture of Rh/Al$_2$O$_3$ and 5% Ru/Al$_2$O$_3$ catalyst (RH:Ru = 7:1).

| Run | Catalyst | Use | Rh/Al$_2$O$_3$ Catalyst Weight as % MDA | Conversion (%) | T95 | PACM (%) | ½ PACM (%) | PACM-Secondary Amines (%) | Deaminated Product (%) | MDA (%) |
|---|---|---|---|---|---|---|---|---|---|---|
| 1 | 2.8% Rh/kappa-Al$_2$O$_3$ | 1 | 1.5 | 99 | 89 | 87.9 | 2.8 | 7.8 | 1.5 | 0 |
|  |  | 2 |  | 99 | 87 | 88.1 | 1.8 | 8.8 | 1.3 | 0 |
| 2 | 2.2% Rh/kappa-Al$_2$O$_3$ | 1 | 1.5 | 99 | 103 | 88.6 | 1.4 | 8.5 | 1.6 | 0 |
|  |  | 2 |  | 99 | 101 | 87.9 | 2.8 | 8.9 | 0.4 | 0 |
| 3 | 1.0% Rh/kappa-Al$_2$O$_3$ | 1 | 1.5 | 99 | 125 | 84.3 | 2.8 | 12.0 | 0.9 | 0 |
|  |  | 2 |  | 95 | 150 | 74.5 | 11.4 | 13.0 | 1.1 | 0 |
| 4 | 4% Rh/gamma-Al$_2$O$_3$ | 1 | 1.5 | 98 | 160 | 86.7 | 3.6 | 8.4 | 1.3 | 0 |
| 5 | 4% Rh/gamma-Al$_2$O$_3$ | 1 | 1.5 | 98 | 140 | 92.2 | 3.2 | 3.6 | 1.1 | 0 |
|  |  | 2 |  | 98 | 105 | 90.8 | 4.1 | 4.1 | 1.0 | 0 |
| 6 | 2.5% | 1 | 1.5 | 99 | 120 | 86.8 | 3.0 | 9.3 | 0.9 | 0 |

TABLE 2-continued

Effect of Rhodium Loading on Activity of Kappa Alumina Catalyst
Hydrogenation of 50% MDA/THF$^a$ at 180° C. and 850 psi pressure using
a physical mixture of Rh/Al$_2$O$_3$ and 5% Ru/Al$_2$O$_3$ catalyst (RH:Ru = 7:1).

| Run | Catalyst | Use | Rh/Al$_2$O$_3$ Catalyst Weight as % MDA | Conversion (%) | T95 | PACM (%) | ½ PACM (%) | PACM-Secondary Amines (%) | Deaminated Product (%) | MDA (%) |
|---|---|---|---|---|---|---|---|---|---|---|
|  | Rh/gamma-Al$_2$O$_3$ | 2 |  | 65 | 150$^b$ | 28.3 | 55.3 | 8.1 | 0.8 | 7.5 |

$^a$Time for 95% conversion
$^b$Time for 65% conversion

Previously, the activity of different phases of alumina was compared and it was concluded that the Rh/kappa-alumina catalyst was twice as active as the gamma-alumina supported catalyst. The rhodium/kappa-alumina catalyst had 2.8% rhodium compared to 4% Rh with the gamma-alumina supported catalyst. These catalyst tests were tested by increasing the catalyst weight of 2.8% Rh/kappa-Al$_2$O$_3$ catalyst such that both catalysts were tested on an equal rhodium basis.

To compare the catalysts on an equal weight basis, the catalysts were tested at 1.5% of MDA. Table 2 compares the activity of a 2.8% Rh/kappa-Al$_2$O$_3$ catalyst to two commercial 4% Rh/gamma-Al$_2$O$_3$ catalysts. Clearly, the 2.8% Rh/kappa-Al$_2$O$_3$ catalyst with 30% lower rhodium is much more active than the commercial 4% Rh/gamma-Al$_2$O$_3$ catalyst. The gamma-alumina catalyst increases activity from first to second use and, therefore, comparison of these catalysts should be done on the basis of the second use. Comparison of rows 2 and 9 of Table 2 clearly show that the kappa-alumina supported catalyst with 30% lower rhodium is about 20% more active than the gamma-alumina catalyst.

A 1% and a 2.2% Rh/kappa-alumina catalyst were prepared and tested for MDA hydrogenation, and these catalysts had high activity. The 1% Rh/kappa-alumina catalyst was only about 45% less active than the commercial 4% Rh/gamma-A$_2$O$_3$ catalyst. The 2.2% Rh/kappa-alumina catalyst had similar activity to the commercial 4% Rh/gamma-A$_2$O$_3$ catalyst. Table 2 also has results for the hydrogenation of MDA with 2.5% Rh/gamma-Al$_2$O$_3$ catalyst. The 2.5% Rh/gamma-A$_2$O$_3$ catalyst has similar activity to the 1% Rh/kappa-alumina catalyst. In the second use, the 2.5% Rh/gamma-Al$_2$O$_3$ catalyst undergoes severe deactivation. These results also show that the activity of the 4% Rh/gamma-Al$_2$O$_3$ catalyst can be matched by the kappa-alumina supports having rhodium loading between 2.2% and 2.7%.

EXAMPLE 4

Catalyst Life Studies

Catalyst life studies were carried out for a series of catalysts. The catalyst was a physical mixture of Rh/Al$_2$O$_3$ (2.8 g) and Ru/Al$_2$O$_3$ (0.3 g). However, to each of these catalysts was added LiOH in three stages. It was added as 1% LiOH (as a percent of catalyst weight) in the second use, 2% in the third use and 1% in the fourth use. Other conditions and results are set forth in Table 3.

TABLE 3

Hydrogenation of 400 g of 50% MDA/THF in a 1-liter autoclave reactor at 165° C. and 850 psi pressure.

| Use | Catalyst | LiOH$^a$ wt % | Temp | Conv | Time at$^b$ Temp | Time for 95% Conv | PACM | t/t | ½ PACM | Deaminated Product | Secondary Amines |
|---|---|---|---|---|---|---|---|---|---|---|---|
| | | | | Life Study A | | | | | | | |
| 1 | 2.8 g of 2.7% Rh/kappa Al$_2$O$_3$ + 0.3 g of 5% Ru/Al$_2$O$_3$ | 0 | 165° C. | 97.7 | 228 | 192 | 86.9 | 15.3 | 4.6 | 0.8 | 7.6 |
| 2 | | +1% | 165° C. | 97.4 | 179 | 152 | 84.7 | 15.9 | 5.2 | 1.0 | 9.2 |
| 3 | | +2% | 165° C. | 97.7 | 164 | 141 | 85.3 | 16.5 | 4.7 | 0.9 | 9.2 |
| 4 | | +1% | 165° C. | 98.3 | 161 | 128 | 91.9 | 19.4 | 3.4 | 0.7 | 4.1 |
| 5 | | 0 | 165° C. | 97.8 | 164 | 135 | 93.9 | 23.9 | 4.4 | 0.5 | 1.3 |
| 6 | | 0 | 165° C. | 97.0 | 180 | 153 | 93.1 | 26.2 | 6.1 | 0.3 | 0.6 |
| 7 | | 0 | 165° C. | 98.1 | 172 | 140 | 94.3 | 25.4 | 3.9 | 0.5 | 1.3 |
| 8 | | 0 | 165° C. | 98.1 | 171 | 134 | 94.4 | 25.4 | 3.9 | 0.5 | 1.2 |
| | | | | Life Study B | | | | | | | |
| 1 | 2.8 g of 4%$^c$ Rh/gamma Al$_2$O$_3$ + 0.3 g of 5% Ru/Al$_2$O$_3$ | 0 | 165° C. | 100 | 244 | 208 | 96.0 | 16.3 | 0 | 0.6 | 3.8 |
| 2 | | +1% | 165° C. | 98.9 | 172 | 134 | 92.3 | 15.2 | 2.3 | 0.7 | 4.7 |
| 3 | | +2% | 165° C. | 98.8 | 161 | 123 | 91.6 | 15.7 | 2.4 | 0.8 | 5.3 |
| 4 | | +1% | 165° C. | 98.3 | 176 | 143 | 93.2 | 18.0 | 3.4 | 0.6 | 2.8 |
| 5 | | 0 | 165° C. | 98.6 | 200 | 160 | 95.8 | 20.6 | 2.8 | 0.4 | 1.0 |
| 6 | | 0 | 165° C. | 98.5 | 200 | 161 | 95.6 | 22.1 | 3.1 | 0.3 | 1.0 |

TABLE 3-continued

Hydrogenation of 400 g of 50% MDA/THF in a 1-liter autoclave reactor at 165° C. and 850 psi pressure.

| Use | Catalyst | LiOH[a] wt % | Temp | Conv | Time at[b] Temp | Time for 95% Conv | PACM | t/t | ½ PACM | Deaminated Product | Secondary Amines |
|---|---|---|---|---|---|---|---|---|---|---|---|
| 7 | | 0 | 165° C. | 98.7 | 200 | 157 | 95.8 | 21.4 | 2.7 | 0.4 | 1.1 |

[a] added as a 10% aqueous solution
[b] time for the given conversion
[c] purchased from Engelhard Corporation Life studies were conducted to compare the activity of the 2.8% Rh/kappa-alumina catalyst to one of the best 4% Rh/gamma-Al$_2$O$_3$ commercial catalyst. During these life studies, the catalyst weight, temperature and pressure were kept constant. The salient features of this life study are listed below.

Kappa-alumina catalyst, with 30% lower rhodium, has an activity similar to the gamma-alumina catalyst.

Kappa-alumina catalyst had an excellent, stable activity through eight uses.

The level of secondary amines were dropped below 1% by adding aqueous LiOH to the feed. The drop in secondary amines was not accompanied by a drop in the rate.

Deaminated product and the t/t isomer content was similar in both catalysts.

The term "time at temp" in Table 3 refers to the time taken for a given conversion and T$_{95}$ is the time taken for 95% conversion. T$_{95}$ was calculated from a combination of GC data and ballast pressure drop. With a 2.8% Rh/kappa-Al$_2$O$_3$ catalyst, the average T$_{95}$ is 147 min (8 uses), and the 4% Rh/gamma-Al$_2$O$_3$ catalyst, the average T$_{95}$ is 155 min (7 uses). Clearly, the advantage of the kappa-alumina catalyst is the lower rhodium usage. The 2.8% Rh/kappa-alumina catalyst which has 30% lower rhodium has an activity and selectivity to PACM similar to the gamma-alumina catalyst. The second important feature of the catalyst is its stable activity during 8 uses.

Also shown in Table 3, the level of secondary amines dropped to about 1% by the fifth use and did not change thereafter. Table 3 also gives the variation of the t/t isomer with re-use of the catalyst. With the kappa alumina catalyst, the t/t isomer content averaged 21% (8 uses) compared to 18.4% average (7 uses) with gamma-alumina catalyst. The level of deaminated PACM is low and falls within the accepted range.

We claim:

1. In a process for the catalytic hydrogenation of aromatic amines to their ring hydrogenated counterparts, by contacting the aromatic amine with hydrogen in the presence of a catalyst, the improvement which comprises effecting said hydrogenation in the presence of a catalyst comprising rhodium carried on an alumina support, said alumina support being kappa.

2. The process of claim 1 wherein the aromatic amine is represented by the formulas:

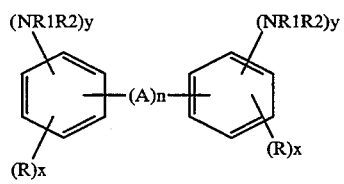

I

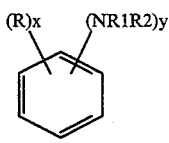

II wherein R is hydrogen or C$_{1-6}$ aliphatic, R1 and R2 are hydrogen or C$_{1-6}$ aliphatic, A is C$_{1-4}$ or NH, n is 0-1, x is 1-3 and y is 1 to 2 except the sum of the y groups in Formula I may be 1.

3. The process of claim 2 wherein said aromatic amine is represented by formula I.

4. The process of claim 3 wherein the catalyst is present in an amount from about 0.1 to 10% by weight of the aromatic amine and the rhodium is present in an amount from 1 to 12 weight parts per 100 weight parts alumina.

5. The process of claim 4 wherein R1 and R2 are hydrogen.

6. The process of claim 5 wherein R is H or methyl.

7. The process of claim 6 wherein n is 0.

8. The process of claim 6 wherein A is —CH$_2$—, R is H, and n is 1.

9. The process of claim 8 wherein each y is 1.

10. The process of claim 9 wherein hydrogenation is conducted at a hydrogen pressure from about 200 to 1500 psig.

11. The process of claim 10 wherein the catalyst system comprises rhodium and ruthenium and the weight ratio of rhodium to ruthenium, as metal, is from about 1 to 12.

12. In a process for the catalytic hydrogenation of crude methylenedianiline containing up to about 15% of oligomer by weight to bis(4-aminocyclohexyl)methane, which comprises hydrogenating the methylenedianiline in the presence of a catalyst system, the improvement which comprises effecting said hydrogenation in the presence of a catalyst comprising rhodium and ruthenium, said catalyst present as a physical admixture, with at least the rhodium component of the catalyst system being carried on a support of kappa-alumina.

13. The process of claim 12 wherein the catalyst system comprising rhodium and ruthenium is present in an amount of from 1 to 12 weight parts rhodium/weight part ruthenium, and the amount of catalyst based on methylenedianiline is from 0.5 to 5% by weight.

14. The process of claim 1 wherein said aromatic amine is represented by formula II.

15. The process of claim 14 wherein the catalyst system comprises rhodium in an amount from 1 to 12 weight parts per 100 weight parts alumina.

16. The process of claim 15 wherein hydrogenation is conducted at a hydrogen pressure from about 200 to 1500 psig.

17. The process of claim 16 wherein the catalyst is present in an amount from about 0.1 to 10% by weight of the aromatic amine.

18. The process of claim 17 wherein R1 and R2 are hydrogen.

19. The process of claim 17 wherein R is methyl, ethyl, or tert-butyl.

20. The process of claim 19 wherein y is 2.

21. The process of claim 20 wherein the pressure is from about 200 to 1500 psig.

22. The process of claim 21 wherein said aromatic amine is 2,4- or 2,6-tert-butyl-toluenediamine.

23. The process of claim 21 wherein said aromatic amine is 1-methyl-diethyl 2,4- or 2,6-diaminobenzene.

* * * * *